US00PP34453P2

(12) United States Plant Patent
Yunquan et al.

(10) Patent No.: US PP34,453 P2
(45) Date of Patent: Jul. 26, 2022

(54) ***ASPLENIUM* PLANT NAMED 'YUASPGIO'**

(50) Latin Name: *Asplenium antiquum*
Varietal Denomination: 'YUASPGIO'

(71) Applicant: Guangzhou Jinxiu Horticulture Development Co., Ltd, Guangzhou (CN)

(72) Inventors: Xianyu Yunquan, Guangzhou (CN); Huang Ziwen, Guangzhou (CN)

(73) Assignee: Guangzhou Jinxiu Horticulture Development Co., Ltd, Guangzhou (CN)

( * ) Notice: Subject to any disclaimer, the term of this patent is extended or adjusted under 35 U.S.C. 154(b) by 0 days.

(21) Appl. No.: 17/803,226

(22) Filed: Mar. 21, 2022

(51) Int. Cl.
*A01H 5/00* (2018.01)

(52) U.S. Cl.
USPC ..... Plt./379

(58) Field of Classification Search
USPC ..... Plt./379
See application file for complete search history.

*Primary Examiner* — Annette H Para
(74) *Attorney, Agent, or Firm* — Samuel R. McCoy, Jr.

(57) ABSTRACT

A new and distinct *Asplenium antiquum* cultivar named 'YUASPGIO' which is characterized by a relatively fast rate of growth, improved cold hardiness and heat tolerance, an abundance of broad, dark green leaves with deeply incised and moderately undulating margins, and the stability of these characteristics from generation to generation.

3 Drawing Sheets

Latin name of the genus and species: The Latin name of the genus and species of the novel variety disclosed herein is *Asplenium antiquum.*

Variety Denomination: The inventive variety of *Asplenium antiquum* disclosed herein has been given the variety denomination 'YUASPGIO'.

BACKGROUND OF THE INVENTION

Parentage: 'YUASPGIO' originated as a sporeling selection of an unnamed *Asplenium antiquum* plant (not patented) which was discovered at a commercial greenhouse in Guangzhou, China. In September of 2012, the inventors discovered several plants growing amongst a cultivated population of unnamed, spore-propagated *Asplenium antiquum* plants which exhibited unique foliage and growth habits, as well as improved vigor, relative to other members of the population and known antecedents. Through multiple subsequent cycles of spore propagation and reselection, over the course of several years and comprising more than 10,000 individual plants, a small number of sporelings were identified by the inventors that both retained the unique characteristics of the plants first observed in 2012 and were also capable of asexual reproduction without suffering high mortality rates. The inventors then selected one plant from this small group of plants that they determined to be the most unique and the most vigorous. After confirmation of the distinctness and stability of the characteristics first observed, the new variety was finally selected in June of 2018 and given the denomination 'YUASPGIO'.

Asexual Reproduction: Asexual reproduction of the new cultivar 'YUASPGIO', by way of mericloning, was first initiated in 2018 at a commercial laboratory in Burgh-Haamstede, The Netherlands. Through at least nine subsequent generations, the unique features of this cultivar have proven to be stable and true to type.

SUMMARY OF THE INVENTION

The cultivar 'YUASPGIO' has not been observed under all possible environmental conditions. The phenotype may vary somewhat with variations in environment such as temperature, day length, and light intensity, without, however, any variance in genotype. The following traits have been repeatedly observed and are determined, to be the unique characteristics of 'YUASPGIO'. These characteristics in combination distinguish 'YUASPGIO' as a new and distinct *Asplenium antiquum* cultivar:

1. *Asplenium* 'YUASPGIO' exhibits an abundance of foliage growing upward and outward in a basal rosette; and
2. *Asplenium* 'YUASPGIO' exhibits improved plant vigor and a relatively fast growth rate; and
3. *Asplenium* 'YUASPGIO' exhibits improved cold hardiness and heat tolerance; and
4. *Asplenium* 'YUASPGIO' exhibits broad, dark green leaves with a coriaceous texture and irregular, deeply incised leaf margins with moderate undulation.

BOTANICAL DESCRIPTION OF THE PLANT

Figure 1:
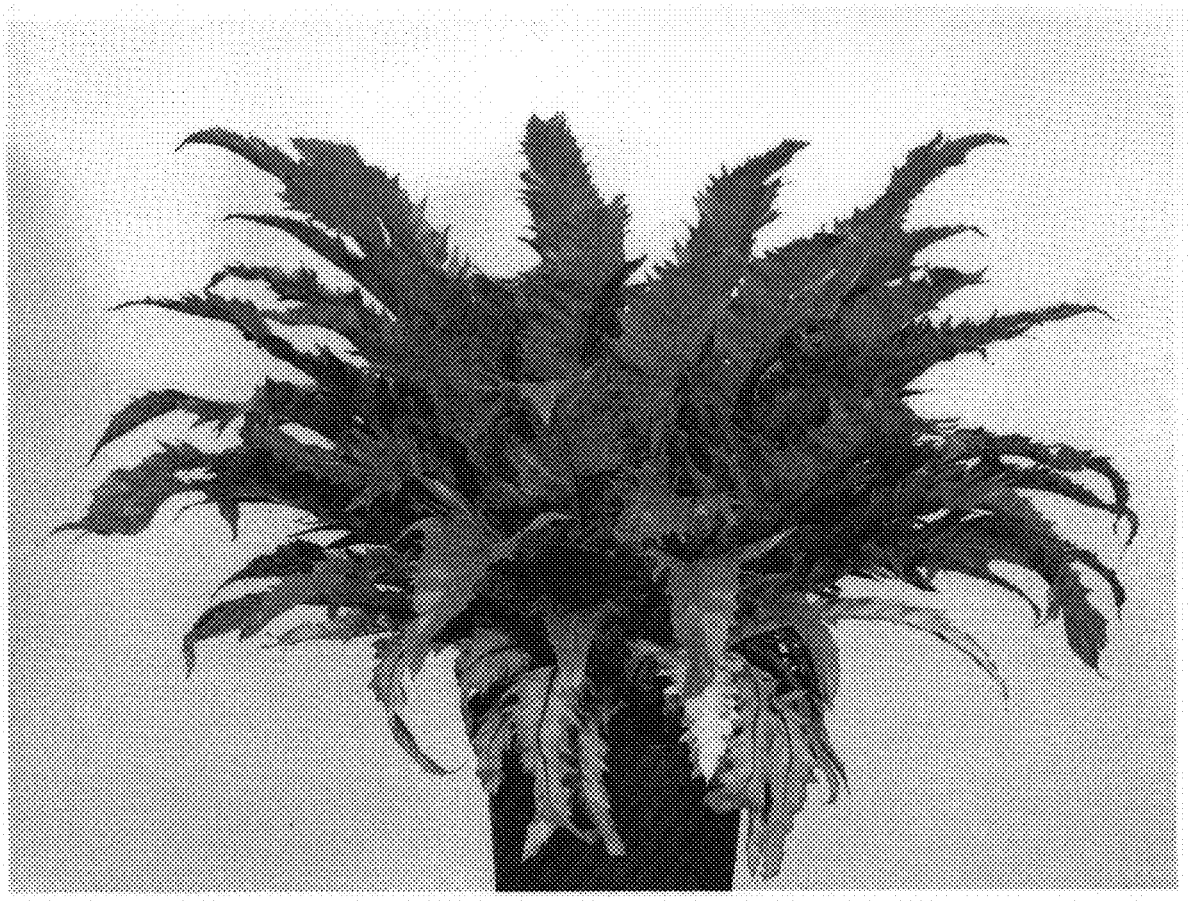
FIG. 1 illustrates, as nearly true as it is reasonably possible to make the same in color photographs of this type, an exemplary plant of 'YUASPGIO' grown in a commercial greenhouse in Burgh-Haamstede, The Netherlands. This plant is approximately 12-month-old, shown planted in a 25 cm container.
Figure 2:
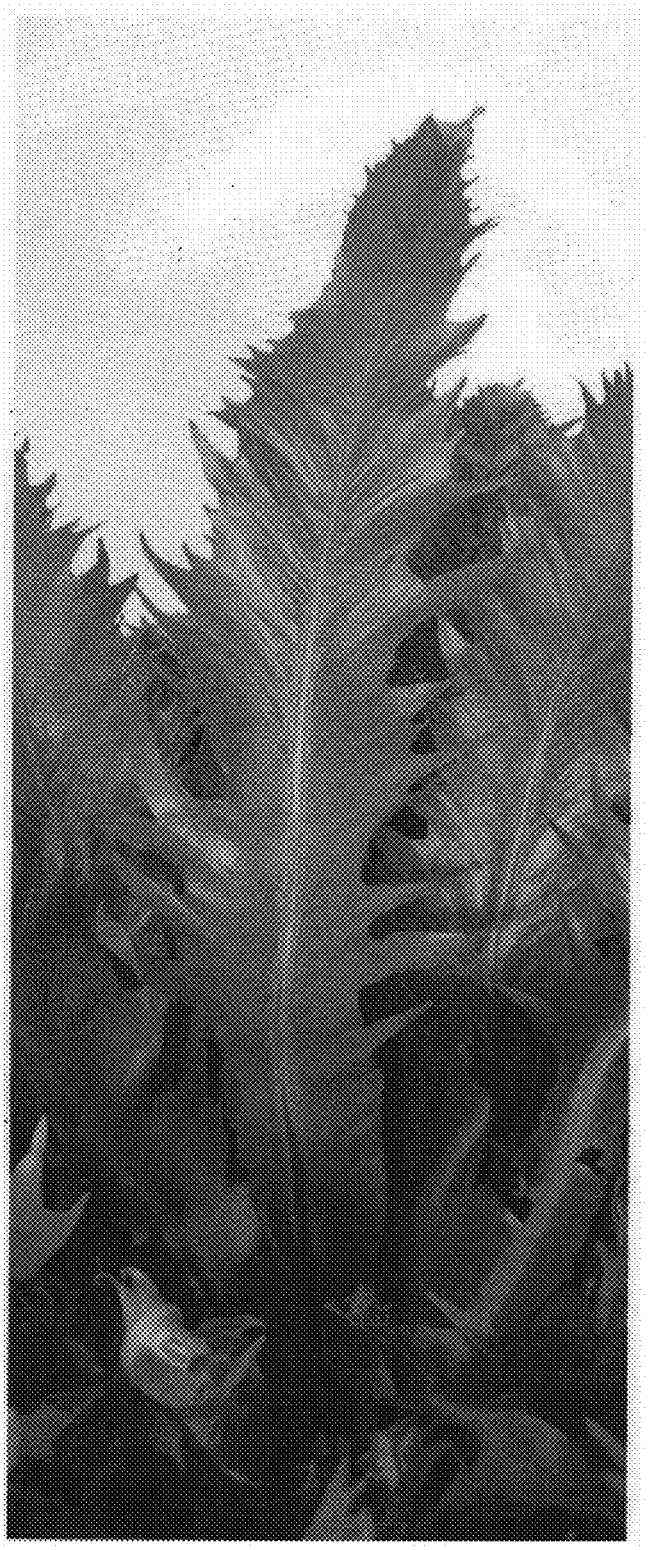
FIG. 2 illustrates, as nearly true as it is reasonably possible to make the same in color photographs of this type, the adaxial surface of the mature foliage of 'YUASPGIO'.
Figure 3:
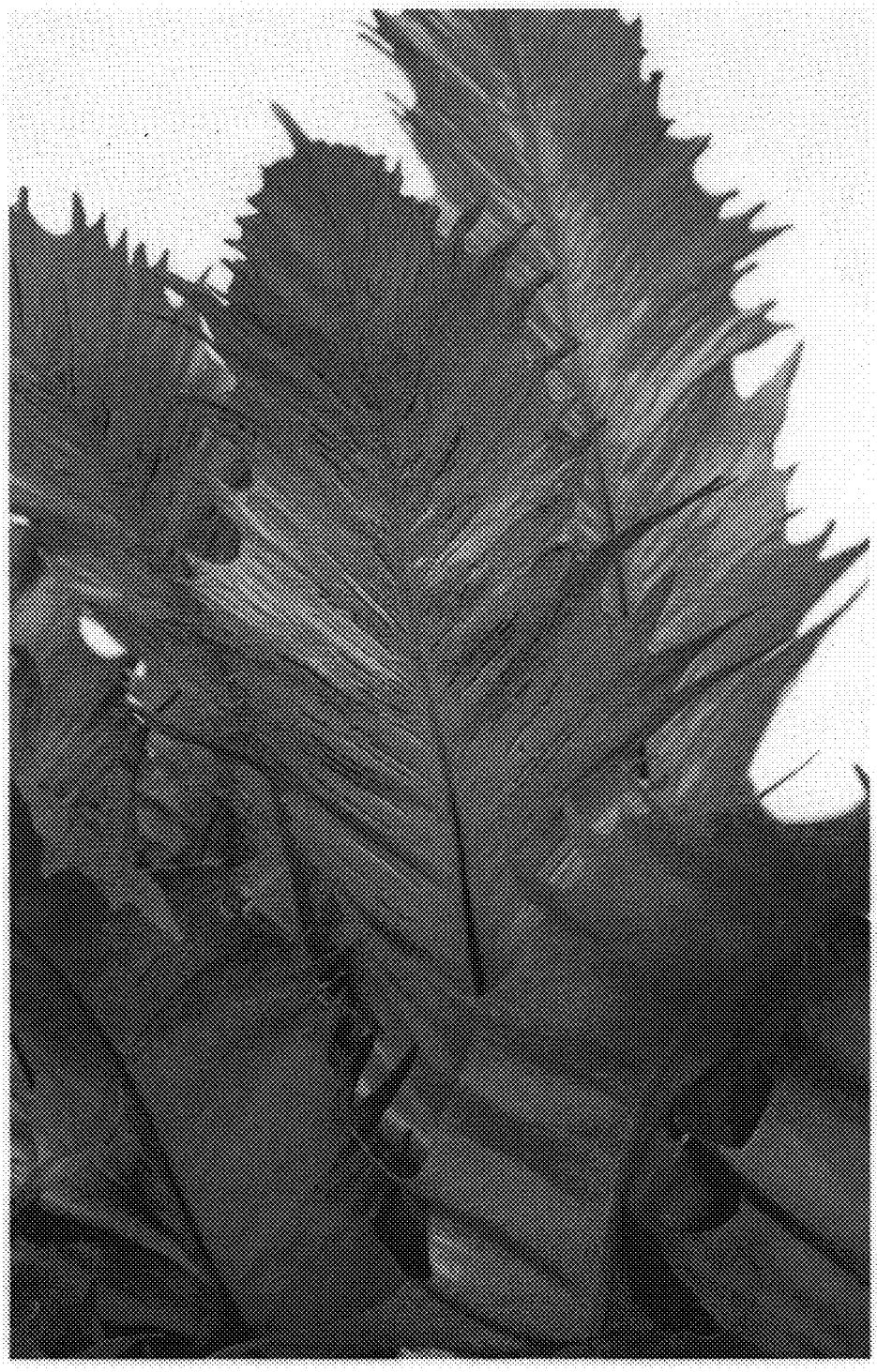
FIG. 3 illustrates, as nearly true as it is reasonably possible to make the same in color photographs of this type, the abaxial surface of the mature foliage of 'YUASPGIO'.

The following observations and measurements made in September of 2021 describe averages from a sample set of six specimens of 12-month-old 'YUASPGIO' plants grown in 25 cm nursery containers at a greenhouse in Burgh-Haamstede, The Netherlands. Plants were produced using conventional greenhouse production protocols for *Asplenium* sp. which consisted of growing plants underneath shade cloth, irrigation by way of ebb and flood growing benches, and liquid fertilizer applications as needed. Temperatures ranged from approximately 5 to 15 degrees Celsius during the day and 1 to 12 degrees Celsius at night. No chemical pest control measures were utilized. No photoperiodic treatments or artificial light was given to the plants.

Those skilled in the art will appreciate that certain characteristics will vary with older or, conversely, with younger plants. 'YUASPGIO' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'YUASPGIO' and a comparison with the parent and closest known comparator are provided below.

Plant description:

*Growth habit*.—Densely-foliaged herbaceous perennial fern with foliage growing in a basal rosette.

*Plant profile*.—Globular.

*Height from soil level to top of foliar plane*.—49.7 cm.

*Plant spread*.—Average of 99.5 cm.

*Growth rate*.—Moderately fast growing.

*Plant vigor*.—Moderately vigorous to vigorous.

*Propagation*.—Type — Mericloning. Time to initiate roots — Approximately 80 days at about 25 degrees Celsius. Crop time — Approximately 26 weeks from propagation to a marketable plant.

*Disease and pest resistance or susceptibility*.—Not any more or less susceptible to pests or diseases known to effect *Asplenium antiquum*.

*Environmental tolerances*.—Adapt to, at least, USDA Zones 10 to 13 and temperatures as high as 35 degrees Celsius; high tolerance to rain; moderate tolerance to wind.

Root system:

*General*.—Fine, well-branched fibrous roots.

*Color*.—Brown, nearest to 200B.

Foliage:

*Arrangement*.—Alternate; growing in basal rosettes.

*Division*.—Simple.

*Quantity*.—Approximately 98 leaves per rosette, of which approximately 40 percent are old, desiccated.

*Dimensions*.—54:9 cm long and 18.4 cm wide, on average.

*Shape*.—Narrow elliptic to narrowly oblong.

*Aspect*.—Flat.

*Attitude*.—Approximately 50 degrees to vertical.

*Apex*.—Apiculate to aristate.

*Base*.—Truncate.

*Margin*.—Irregularly incised and occasionally deeply incised, giving the appearance of a lobed leaf margin; leaves are moderately undulated.

*Pubescence, texture and luster of adaxial surface*.—Glabrous, smooth, and very glossy. In juvenile foliage, the base of the main vein is moderately to densely covered with fibrous greyed-brown hairs, nearest to RHS 199B, with an average length of 0.4 cm.

*Pubescence, texture and luster of abaxial surface*.—Glabrous, smooth, and glossy. In juvenile foliage, the base of the main vein is moderately to densely covered with fibrous greyed-brown hairs, nearest to RHS 199B, with an average length of 0.4 cm.

*Color*.—Juvenile foliage, adaxial surface — Yellow-green, nearest to RHS 144A. Juvenile foliage, abaxial surface — Yellow-green, nearest to in between RHS 144A and 144B. Mature foliage, adaxial surface — Green, nearest to a mixture of RHS 137B and 143B but slightly darker. Mature foliage, abaxial surface — Nearest to a mixture of green and yellow-green, RHS 138A and 146A.

*Venation*.—Pinnate.

*Venation color, adaxial surface*.—The main vein is yellow-green, nearest to RHS 144A, and is heavily suffused with black towards the proximal end, nearest to RHS 203C. Secondary veins are in between green, nearest to a mixture of RHS 137B and 143B but slightly darker.

*Venation color, abaxial surface*.—The main vein is brown, nearest to in between RHS 200A and 200B, and is heavily suffused with black towards the proximal end, nearest to RHS 203C. Secondary veins are nearest to a mixture of green and yellow-green, RHS 138A and 146A.

*Petiole*.—Aspect — Elliptic. Length — 1.2 cm. Vertical height — 0.9 cm. Width — 0.6 cm. Texture — Smooth and glabrous, with the exception of the base of juvenile petioles which are moderately to densely covered with fibrous greyed-brown hairs, nearest to RHS 199B, with an average length of 0.4 cm. Luster — Adaxial surface is moderately glossy; abaxial surface is glossy. Strength — Strong. Color, adaxial surface — Black, nearest to RHS 203C, and margined yellow-green, nearest to RHS 144B. Color, abaxial surface — Black, nearest to RHS 203B, and margined yellow-green, nearest to RHS 144B.

Sori:

*Quantity of sori per leaf*.—84 rows of sori; 42 rows on either side of the main vein.

*Quantity of sori per plant*.—More than 1,500; an average of 21 leaves per plant carrying sori.

*Arrangement*.—Linear.

*Length*.—1.8 cm; varying from 0.4 cm to 3.5 cm.

*Diameter*.—0.1 cm.

*Color*.—Sori — Grey-brown, nearest to RHS 199A. Spores — Greyed-orange, nearest to RHS 166B.

COMPARISONS WITH THE PARENT PLANT

Plants of the new cultivar 'YUASPGIO' differ from the parent, an unnamed *Asplenium antiquum* plant (not patented), by the characteristics described in Table 1.

TABLE 1

| Characteristic | 'YUASPGIO' | The parent. |
|---|---|---|
| Plant vigor. | More vigorous; lower mortality rates when asexually propagated. | Less vigorous; higher mortality rates when asexually propagated. |

TABLE 1-continued

| Characteristic | 'YUASPGIO' | The parent. |
|---|---|---|
| Rate of growth. | Faster than the parent. | Slower than 'YUASPGIO'. |
| Cold hardiness. | More cold hardy than the parent. | Less cold hardy than 'YUASPGIO'. |
| Heat tolerance. | More heat resistant than the parent. | Less heat resistant than 'YUASPGIO'. |

COMPARISONS WITH THE MOST SIMILAR *ASPLENIUM* CULTIVAR KNOWN TO THE INVENTOR

Plants of the new cultivar 'YUASPGIO' are most similar to the commercial cultivar, *Asplenium nidus* 'Campio' (U.S. Plant Pat. No. 30,949). A comparison of 'YUASPGIO' with *Asplenium* 'Campio' is described in Table 2.

TABLE 2

| Characteristic | 'YUASPGIO' | 'Campio' |
|---|---|---|
| Plant size. | Larger than 'Campio'. | Smaller than 'YUASPGIO'. |
| Foliage size. | Larger than 'Campio'. | Smaller than 'YUASPGIO'. |
| Foliage abundance. | More abundant than 'Campio'. | Less abundant than 'YUASPGIO'. |
| Foliage shape. | Narrow elliptic to narrowly oblong. | Oblanceolate. |
| Foliar margin undulation. | Moderately undulated. | Slightly undulate. |

That which is claimed is:

1. A new and distinct variety of *Asplenium antiquum* plant named 'YUASPGIO', substantially as described and illustrated herein.

* * * * *